United States Patent [19]

Raynolds et al.

[11] Patent Number: 4,785,133

[45] Date of Patent: Nov. 15, 1988

[54] PROCESS FOR THE PREPARATION OF ALKYL 3-ALKOXYPROPIONATES

[75] Inventors: Peter W. Raynolds; Glenn C. Jones, both of Kingsport, Tenn.

[73] Assignee: Eastman Kodak Company, Rochester, N.Y.

[21] Appl. No.: 104,454

[22] Filed: Oct. 5, 1987

[51] Int. Cl.$^4$ .............................................. C07C 69/66
[52] U.S. Cl. .................................. 560/187; 502/150
[58] Field of Search .................... 560/182; 502/150

[56] References Cited

U.S. PATENT DOCUMENTS

| | | | |
|---|---|---|---|
| 2,436,286 | 2/1948 | Brooks | 560/187 |
| 2,910,503 | 10/1959 | Fox | 560/187 |
| 3,049,560 | 8/1962 | Enk et al. | 560/187 |
| 3,052,713 | 9/1962 | Jowitt | 560/187 |

FOREIGN PATENT DOCUMENTS

| | | | |
|---|---|---|---|
| 475852 | 8/1951 | Canada | 560/187 |
| 612378 | 1/1961 | Canada | 560/187 |
| 685185 | 4/1964 | Canada | 560/187 |
| 923341 | 4/1963 | United Kingdom | 560/187 |

OTHER PUBLICATIONS

Sorm et al, *Chemical Abstracts*, vol. 49, No. 175C (1955).

*Primary Examiner*—Paul F. Shaver
*Assistant Examiner*—Bruce D. Gray
*Attorney, Agent, or Firm*—J. Frederick Thomsen; William P. Heath, Jr.

[57] ABSTRACT

Disclosed is an improved process for the preparation of alkyl 3-alkoxypropionates containing at least seven carbon atoms by the reaction of dialkoxymethane containing five or more carbon atoms with a ketene in the presence of a catalytic amount of the reaction product of an alkylcarboxylic acid anhydride and concentrated or fuming sulfuric acid.

6 Claims, No Drawings

PROCESS FOR THE PREPARATION OF ALKYL 3-ALKOXYPROPIONATES

DESCRIPTION

This invention concerns a novel process for the preparation of ether-ester compounds especially useful as solvents in the formulation of coating compositions. More particularly, this invention concerns a novel process for the preparation of alkyl 3-alkoxypropionates, having at least seven carbon atoms.

The synthesis of alkyl 3-alkoxypropionates by the reaction of a dialkoxymethane with a ketene is well known in the literature as shown by U.S. Pat. Nos. 2,436,286, 2,910,503 and 3,052,713 and Chem. Listy, 47, 413 (1953) abstracted at C.A. 49: 175C. Although the cited references suggest that various proton and Lewis acids may be used to catalyze the reaction, only the use of boron trifluoride and zinc chloride have been shown to effect the formation of alkyl 3-alkoxypropionates having at least seven carbon atoms to any significant degree. Although useful in the reaction, boron trifluoride is expensive and presents corrosion, toxicity and waste disposal problems as compared to most proton acids. Zinc chloride is a poor catalyst for the reaction and also poses disposal problems. Two other Lewis acids have been found to be unsatisfactory. Boron triacetate is inactive while the extremely active aluminum chloride gives a complex mixture of products at low conversion.

U.S. Pat. No. 2,436,286 discloses the reaction of ketene in excess methylal, i.e., dimethoxymethane, to obtain methyl 3-methoxypropionate. Although dimethoxymethane is significantly more reactive than higher dialkoxymethanes, the conversion of ketene to methyl 3-methoxypropionate (21.8%) was poor due to the catalyst (concentrated sulfuric acid) employed even though a substantial amount (5.15%) was present.

Many of the more common proton acids have been found to be unsuitable for catalyzing the reaction of a ketene and dialkoxymethane. Concentrated (97%) sulfuric acid failed to catalyze the reaction even when added below the surface to diethoxymethane saturated with ketene. Both arylsulfonic acids and a sulfonic acid ion exchange resin (Amberlyst 15) gave no reaction. Hydrohalogen acids are not suitable since they are corrosive and are known to react with ketene to give acid halides.

We have discovered that the reaction product of a carboxylic anhydride and concentrated sulfuric acid or especially fuming sulfuric acid (oleum) is an excellent catalyst for the preparation of alkyl 3-alkoxypropionates containing at least seven carbon atoms by the reaction of a dialkoxymethane containing five or more carbon atoms with a ketene according to known procedures. The activity of such acidic catalysts in the manufacture of such alkyl 3-alkoxypropionates is good to excellent and their use does not involve any unusual disposal or toxicity problems. Furthermore, the acidic catalysts employed in our novel process are relatively inexpensive and require no unusual handling procedures. While the anhydride-sulfuric acid reaction products, as well as certain other acidic compounds referred to hereinabove, are characterized as catalysts for the reaction, they are consumed to a significant degree in the process of preparing the alkyl 3-alkoxypropionates, i.e., all catalysts acidic enough to cause a reaction also react with the dialkoxymethane reactant or alcohol derived therefrom to give inactive esters or complexes.

U.S. Pat. No. 2,521,913 discloses the reaction of concentrated sulfuric acid and acetic anhydride at 80° C. followed by removal of the acetic acid formed by distillation under reduced pressure. The material that was obtained was characterized as acetyl sulfoacetic acid and was used as a catalyst in the preparation of unsaturated carboxylic esters by the reaction of enolizable organic compounds with unsaturated monocarbocyclic esters. We prepared acetyl sulfoacetic acid from sulfoacetic acid and found that it did not catalyze the reaction of ketene with dialkoxymethanes. The reaction of acetic anhydride and concentrated sulfuric acid and/or the characterization of the reaction product also are disclosed in Analytical Chemistry, 40, 350 (1968), Compt. rend., 92, 1054 (1881), Rec. Trav. Chim., 7, 27 (1888) and J. Am. Chem. Soc., 62, 1230 (1940).

The process of our invention involves the preparation of alkyl 3-alkoxypropionates containing at least seven carbon atoms by reacting a dialkoxymethane having at least five carbon atoms with a ketene in the presence of the reaction product of a carboxylic acid anhydride and concentrated or fuming sulfuric acid. The reactants and reaction conditions involved in the process of the invention are well known as shown by the references cited hereinabove. The dialkoxymethane reactant has the structure $$R^1OCH_2OR^2$$

wherein $R^1$ and $R^2$ are the same or different alkyl groups of two or more carbon atoms, e.g., alkyl containing from two to about eight carbon atoms. Typically, $R^1$ and $R^2$ represent the same alkyl groups of two to about four carbon atoms such as ethyl, propyl, isopropyl, butyl and isobutyl. Preferably, $R^1$ and $R^2$ are both ethyl.

The ketene compounds which may be used in the process have the general formula

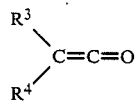

wherein $R^3$ and $R^4$ are hydrogen or the same or different substituent selected from alkyl or aryl groups.

In addition to the substituents which $R^3$ and $R^4$ may represent individually, they also may represent collectively alkylene groups such as pentamethylene, hexamethylene, oxadiethylene, thiadiethylene, etc. Typical alkyl and aryl groups represented by $R^3$ and $R^4$ are methyl, ethyl, propyl, isopropyl, butyl, isobutyl, phenyl and p-tolyl. The preferred reactant is ketene, i.e., wherein each of $R^3$ and $R^4$ is hydrogen.

The temperature at which our novel process may be carried out normally should be in the range of about 10° to 60° C. Operating at temperatures outside of this range gives poor reaction rates and/or poor yields due to the conversion of the ketene to other products or decomposition of the dialkoxymethane reactant. The process preferably is conducted at a temperature in the range of 10° to about 30° C. The ratio of the reactants is not important although the process normally is performed using a stoichiometric excess of the dialkoxymethane reactant to avoid dimerization and polymerization of the ketene reactant. The ratio of reactants present in the reactor at any given time is difficult to determine at any given time because of their reactivity. When the process is conducted in a batch manner the ketene reactant generally is added over a period of time to a mixture of the catalyst in a dialkoxymethane. The ketene addition may be continuous or semi-continuous and should be at a rate sufficient to provide an acceptable conversion of the ketene to the desired alkyl alkoxypropionate product. When performing the process in a continuous manner a stream of a dialkoxymethane containing the catalyst is combined and mixed with a stream of the ketene reactant. The mole ratio of dialkoxymethane to ketene fed to the reactor regardless of the mode of operation may be in the range of about 1:1 to 20:1 although ratios in the range of about 1:1 to about 2:1 normally are used to maximize the conversion of the dialkoxymethane and thereby avoid the disposal or recycle of it.

The acidic compositions used in the process provided by this invention may be prepared by reacting a carboxylic acid anhydride and concentrated sulfuric acid, e.g., greater than about 95 percent sulfuric acid, or oleum, e.g., fuming sulfuric acid containing up to 100 percent sulfur trioxide. Of course, mixtures of concentrated and fuming sulfuric acid may be used if desired. The particular anhydride that may be employed to give an active catalyst is believed to not be important. For example, anhydrides of aryl- and alkylcarboxylic acids containing from about 2 to 8 carbon atoms may be useful. In addition to acetic acid, examples of such acids include propionic, butyric, isobutyric, valeric, caproic, 2-ethylhexanoic, benzoic and p-toluic acids. Since there normally is no advantage in using the higher molecular weight anhydrides, acetic anhydride is preferred. The amounts of concentrated or fuming sulfuric acid and anhydride which may be reacted to give an active catalyst may be varied substantially depending on a number of factors such as the activity desired and the particular materials (grade of sulfuric acid and the anhydride) used. The weight ratio of anhydride to concentrated or fuming sulfuric acid usually will be in the range of 1:5 to 20:1 with a ratio of about 0.7:1 to 1:0.7 being more common. While the temperature used in the preparation of the catalyst can be varied considerably, e.g., from about 0° to 120° C., the exothermic reaction of sulfuric acid or oleum and anhydride is most conveniently carried out in an apparatus designed for efficient heat transfer and cooled in a 30°–60° C. bath.

We have found that the catalytic activity of acidic compositions obtained from concentrated sulfuric acid and an anhydride can be increased simply by ageing the anhydride-sulfuric reaction product at approximately ambient temperature and pressure. We also have discovered that the catalytic activity of the such acidic compositions can be increased significantly if the compositions are heated to a temperature which effects the evolution of gas. Thus, heating the reaction product obtained from acetic anhydride and sulfuric acid to a temperature of about 70° C. or higher, e.g. 105° C., causes the evolution of a considerable amount of gas, primarily carbon dioxide, resulting in a catalyst having significantly greater activity than does the unheated reaction product. Alternatively, the reaction product may be heated under reduced pressure to effect the evolution of gas including the by-product carboxylic acid which is formed when an anhydride and concentrated sulfuric acid are mixed together.

The use of acidic compositions obtained by mixing or reacting an alkylcarboxylic anhydride and oleum in the process provided by my invention gives especially good results. Such compositions exhibit excellent catalytic activity without the necessity of either an ageing or heating step.

The amount of the acidic compositions which may be used in the process provided by my invention can be varied substantially depending, for example, on the activity of the particular acidic composition used, the design of the reactor or reactors, the ratio of reactants, the rate and degree of conversion desired, etc. Typically, about 0.01 to 2.0 weight percent of the acidic compositions based on the weight of the dialkoxymethane reactant will be catalytically effective with amounts in the range of about 0.05 to 0.5 weight percent being preferred. The term "catalyst" is used herein with the understanding that the catalyst has a relatively short life.

The process may be carried out in a batch, semi-continuous or continuous manner. A preferred mode of operation involves a counter-current absorber-reactor wherein the dialkoxymethane compound and catalyst are fed to the upper portion of a packed column and the ketene is fed to the lower portion. As the ketene gas contacts the mixture of dialkoxymethane and catalyst it dissolves in and reacts with the dialkoxymethane to produce the alkyl 3-alkoxypropionate product which is removed from the bottom of the column along with excess dialkoxymethane, any unreacted ketene and catalyst as well as by-products. The column underflow may be refined directly, for example, by distillation with or without prior neutralization. If the column underflow contains a significant amount of ketene, the underflow may be fed to one or more hold-tanks to permit complete reaction of the ketene prior to purifying the crude reaction mixture.

The primary reaction which occurs during the process is represented by the equation:

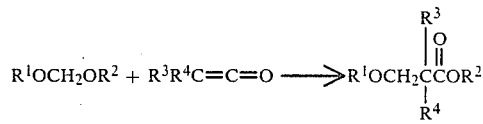

wherein $R^1$, $R^2$, $R^3$ and $R^4$ are defined hereinabove. When $R^1$ and $R^2$ represent different alkyl groups, the product will be a mixture of two or more compounds.

The process is particularly useful for the preparation of ethyl 3-ethoxypropionate by the reaction of diethoxymethane ($R^1=R^2=$ethyl) with ketene ($R^3=R^4=$hydrogen).

An apparatus for the continuous preparation of acidic catalyst compositions was constructed of 316 stainless tubing and Swagelock fittings. A section of ⅛-inch tubing was inserted into a section of ¼-inch tubing and the fittings were affixed to the ends of the ¼-inch tubing to permit cooling water to be circulated through the ⅛-inch tubing and acetic anhydride to be fed to one end and catalyst product to be removed from the opposite end of the ¼-inch tubing. Another fitting for the addition of sulfuric acid was affixed to the exterior tubing slightly downstream from the point of the anhydride feed. Two thermocouples were affixed to the exterior tubing, one approximately six inches downstream from the fitting provided for sulfuric acid addition and the other approximately six inches upstream from the product take-off point. A single coil was formed in the middle section of the tubing which was placed in a water bath so that the acid feed and both thermocouples were positioned below and the anhydride feed and product take-off locations were positioned less than three inches above the surface of the water. During operation cooling water was fed to the internal ⅛-inch tubing and acetic anhydride and sulfuric acid were fed with FMI metering pumps with ¼-inch stainless steel heads (type SSY).

The concentrated sulfuric acid employed was a standard laboratory grade labeled as being 97 percent assay. The fuming sulfuric acid (oleum) employed also was a standard laboratory grade stated to have a sulfur trioxide content of 27–33 percent. The acetic anhydride contained about 0.5 percent acetic acid by gas-liquid chromatography.

Our novel process is further illustrated by the following examples.

EXAMPLE 1

Using the above-described apparatus, a catalyst composition was prepared by feeding 8.3 g/minute acetic anhydride and 10.2 g/minute concentrated sulfuric acid. The temperature of the water bath was 52° C. and the water circulated through the ⅛-inch diameter tubing was 55° C.

A 100 ml three-necked round bottom flask equipped with a dry ice condenser, magnetic stirrer, gas inlet and thermometer was charged with 40 ml of diethoxymethane, 5.0 g of ethyl 3-ethoxypropionate and 1.00 g dodecane (an internal standard for gas-liquid chromatography analysis), and the flask was placed in a 30° C. water bath. Ketene gas, produced by cracking diketene in a 550° C. furnace, was added until the solution became saturated. A portion (0.1143 g) of the catalyst prepared as described above and stored for one week at room temperature, was added on the tip of the thermometer. An exothermic reaction ensued, briefly raising the pot temperature to 80° C. The mixture was kept saturated with ketene for 30 minutes. The mixture was then analyzed by gas-liquid chromatography, and it was found that the 0.1143 g of catalyst had produced 17.3 g of ethyl 3-ethoxypropionate, not including the 5 grams added at the start. This catalyst was thus capable of producing 156 g of ethyl 3-ethoxypropionate for each gram of catalyst.

The remainder of the catalyst composition prepared as described above was heated at 90° C. for four minutes. When tested as described above, the resulting catalyst produced 161 g of ethyl 3-ethoxypropionate per gram of catalyst. The once-heated catalyst composition was then heated at 108° C. for four minutes, causing the evolution of gas. The resulting composition, when tested as described above, produced 197 g of ethyl 3-ethoxypropionate per gram of catalyst.

EXAMPLE 2

Using the above-described apparatus, a catalyst composition was prepared by feeding 8 g/minute acetic anhydride and 5.4 g/minute 27% fuming sulfuric acid. The temperature of the water bath was 52° C. and the water circulated through the ⅛-inch diameter tubing was 55° C. The temperature at the thermocouple proximate the acid feed was 68° C. and at the other thermocouple, 51° C. Approximately 6–7 ml of gas was evolved for each gram of catalyst composition produced.

When evaluated as a catalyst in the preparation of ethyl 3-ethoxypropionate according to the procedure described in Example 1, this catalyst composition produced 304 g of product for each gram of catalyst composition, or 753 g of ethyl 3-ethoxypropionate for each gram of 27% fuming sulfuric acid used to prepare the catalyst.

The activity described in the preceding examples was based on the amount of ethyl 3-ethoxypropionate produced until the catalyst was deactivated.

EXAMPLE 3

A 300 ml, round-bottom, three-necked flask equipped with a magnetic stirrer, thermometer and dropping funnel was charged with 150 g of acetic anhydride and warmed to 70° C. Concentrated sulfuric acid (40 ml, 74 g) was added dropwise at a rate that kept the internal temperature below 83° C. A liquid, believed to consist primarily of acetic acid and acetic anhydride, was distilled at a pot temperature of less than 55° C. and at a pressure of as low as 1 torr. The dark orange product weighed 143 g.

To a 500 ml flask equipped with a magnetic stirrer, thermometer, gas inlet and dry ice condenser was added 200 g of diethoxymethane. Ketene, produced by cracking 83 ml of diketene in a 550° C. hot tube was added to the reaction vessel over a period of two hours. During the addition of ketene, 2.9 g of the acidic composition prepared as described in the preceding paragraph was added in approximately 0.5 g portions. Ketene and catalyst were added to keep the reaction temperature at 40°–45° C. while the reaction vessel was in a 30° C. water bath. The mixture was neutralized with sodium carbonate and product was distilled. Ethyl 3-ethoxypropionate (EEP) was obtained in 92% yield at 90% conversion.

EXAMPLE 4

Acetic anhydride (150 g) is heated to 70° C. and concentrated (97%) sulfuric acid (74 g) is added at a rate that maintains the reaction mixture at a temperature of less than 83° C. Excess acetic anhydride and acetic acid are removed at a pressure of less than 5 mm of mercury which the reaction mixture is maintained at a temperature of less than 55° C. The resulting acidic composition weighed 143 g.

A 100 ml, three-neck, round-bottom flask equipped with a ketene gas inlet, thermometer and positioned in a 30° C. water bath is charged with 30 g of ethoxy-isobutoxymethane (b.p. 127°–129° C.). Ketene gas is introduced above the surface of the liquid and about 0.5 g of the acidic composition prepared as described above is added. The resulting crude reaction mixture consisted of, in addition to minor amounts of impurities and starting materials, a 6:3:1 mixture (integrated peak area by gas chromatography) of ethyl 3-ethoxypropionate, a mixture of ethyl 3-isobutoxypropionate and isobutyl 3-ethoxypropionate, and isobutyl 3-isobutoxypropionate.

EXAMPLE 5

Example 4 is repeated using di-n-propoxymethane (30 g) in place of ethoxy-isobutoxymethane. An exothermic reaction ensued with the internal temperature rising as high as 45° C. Sodium carbonate (1 g) is added to the resulting material and 29.9 g of propyl 3-propoxypropionate is recovered by distillation (b.p. 75° C. at 8 torr).

The invention has been described in detail with particular reference to preferred embodiments thereof, but it will be understood that variations and modification can be effected within the spirit and scope of the invention.

I claim:

1. In a process for the preparation of an alkyl 3-alkoxypropionate containing at least seven carbon atoms which comprises reacting a dialkoxymethane containing at least five carbon atoms with a ketene at a temperature of about 10° to 50° C. in the presence of an acid catalyst, the improvement comprising carrying out the process in the presence of the reaction product of a carboxylic acid anhydride and concentrated or fuming sulfuric acid as the acid catalyst.

2. Process according to claim 1 wherein the anhydride is an alkylcarboxylic acid anhydride having 2 to 8 carbon atoms.

3. Process according to claim 1 for the preparation of ethyl 3-ethoxypropionate which comprises reacting diethoxymethane with ketene in the presence of a catalytic amount of the reaction product of acetic anhydride and oleum.

4. Process for the preparation of an alkyl 3-alkoxypropionate containing at least seven carbon atoms which comprises reacting a dialkoxymethane containing at least five carbon atoms with a ketene at a temperature of about 10° to 60° C. in the presence of about 0.01 to 2.0 weight percent, based on the weight of the dialkoxymethane, of an acidic composition obtained by reacting a carboxylic acid anhydride and concentrated or fuming sulfuric acid.

5. Process for the preparation of an alkyl 3-alkoxypropionate containing at least seven carbon atoms which comprises reacting a dialkoxymethane having the formula $$R^1OCH_2OR^2$$

with ketene at a temperature of about 10° to 30° C. in the presence of about 0.05 to 0.5 weight percent, based on the weight of the dialkoxymethane, of an acidic composition obtained by reacting acetic anhydride and oleum, wherein $R^1$ and $R^2$ are the same alkyl groups of two to about four carbon atoms.

6. Process according to claim 5 wherein the alkyl 3-alkoxypropionate is ethyl 3-ethoxypropionate and the dialkoxymethane is diethoxymethane.

* * * * *